US00PP37790P2

(12) United States Plant Patent
Moucheboeuf

(10) Patent No.: US PP37,790 P2
(45) Date of Patent: Oct. 20, 2026

(54) ***DIANTHUS* PLANT NAMED 'KLEDA28842'**

(50) Latin Name: ***Dianthus* x *allwoodii* hort**
Varietal Denomination: KLEDA28842

(71) Applicant: KLEMM + SOHN GMBH & CO. KG, Stuttgart (DE)

(72) Inventor: Laetitia Moucheboeuf, Exeter (GB)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/359,525

(22) Filed: Oct. 15, 2025

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./273, 275
CPC . A01H 5/02; A01H 5/00; A01H 6/305; A01H 6/30
See application file for complete search history.

(56) References Cited

PUBLICATIONS

Greenhouse Grower Registration for California Spring Trials 2025 Is Now Open, retrieved on Feb. 10, 2026 at https://www.greenhousegrower.com/events/registration-for-california-spring-trials-2025-is-now-open/, 3 pp. (Year: 2025).*
McPherson 2025, Lawn & Garden Retailers Perennials and shrubs standouts from California Spring Trials, retrieved on Feb. 10, 2026 at https://lgrmag.com/article/perennials-and-shrubs-standouts-from-california-spring-trials/, 8 pp. (Year: 2025).*
Plant Haven Scent First Dianthus Lemon Sparkler, retrieved on Feb. 10, 2026 at https://media.planthaven.com/dev/docs/2025/04/Dianthus-SCENT-FIRST®-Lemon-Sparkler-PK.pdf, one page (Year: 2026).*

* cited by examiner

*Primary Examiner* — June Hwu
(74) *Attorney, Agent, or Firm* — Weatherly IP Solutions, LLC; Karen P. Bechtold; James M. Weatherly

(57) ABSTRACT

A new *Dianthus* plant designated 'KLEDA28842' particularly distinguished by numerous petals per flower and a yellow flower color with a moderate amount of light orange stripes, a few pink-red stripes, and a few pink-red speckles on the petals, is disclosed.

1 Drawing Sheet

Genus and species: *Dianthus* x *allwoodii* hort.
Variety denomination: 'KLEDA28842'.

BACKGROUND OF THE NEW PLANT

The present invention comprises a new and distinct variety of *Dianthus*, botanically known as *Dianthus* x *allwoodii* hort. and hereinafter referred to by the variety name 'KLEDA28842'. 'KLEDA28842' originated from a cross pollination between female parent '16.895' (unpatented) and male parent '16.866' (unpatented) in July 2018 in Ashcombe, Dawlish, United Kingdom.

In August 2019, 'KLEDA28842' was selected and in September 2019, 'KLEDA28842' was first vegetatively propagated by vegetative cuttings in Ashcombe, Dawlish, United Kingdom. 'KLEDA28842' was found to reproduce true to type in successive generations of asexual propagation in Ashcombe, Dawlish, United Kingdom via vegetative cuttings.

SUMMARY

The following are the most outstanding and distinguishing characteristics of 'KLEDA28842' when grown under normal horticultural practices in Stuttgart, Germany.

1. Numerous flower petals, and
2. Yellow flower color with a moderate amount of light orange stripes, a few pink-red stripes, and a few pink-red speckles on the petals.

DESCRIPTION OF THE PHOTOGRAPH

This new *Dianthus* plant is illustrated by the accompanying photograph of a 9-month-old plant taken in June 2025 indoor in Dawlish Devon, United Kingdom. The colors shown are as true as can be reasonably obtained by conventional photographic procedures. The photograph is a whole plant photo of 'KLEDA28842' and shows the foliage, buds, and flowers.

DESCRIPTION

The following detailed descriptions set forth the distinctive characteristics of 'KLEDA28842'. The data which define these characteristics were collected from 9-month-old plants in July 2025 indoors in Dawlish, United Kingdom. Color references are to The R.H.S. Colour Chart of The Royal Horticultural Society of London (R.H.S.), 6$^{th}$ edition (2015).

Classification:
*Family.*—Caryophyllaceae.
*Botanical.*—*Dianthus* x *allwoodii* hort.
*Designation.*—'KLEDA28842'.
*Type.*—Perennial carnation.

Parentage:
*Female parent.*—'16.895' (unpatented).
*Male parent.*—'16.866' (unpatented).

Plant:
*Propagation type.*—Vegetative via shoot cuttings.

*Time to produce a rooted young plant.*—5 weeks to produce a rooted plug.
*Root description.*—Fibrous, fine roots, RHS156C.
*Rooting habit shape.*—Fibrous.
*Plant form.*—Compact mounding habit, upright.
*Plant height.*—30.0 cm to 35.0 cm.
*Plant diameter or spread.*—20.0 cm to 23.0 cm.

Lateral branches/stems (shoot before elongation):
*Shape of the branch in cross-section.*—Circular.
*Hollowness of the branch.*—Absent.
*Length.*—11.0 cm to 13.0 cm.
*Diameter.*—0.4 cm.
*Internode length.*—0.5 cm.
*Internode quantity per shoot.*—5 to 6.
*Number of internodes per branch/stem.*—5 to 6.
*Node length.*—0.4 cm.
*Node diameter.*—0.3 cm.
*Texture.*—Smooth.
*Color (in sheathing zone).*—Between RHS 145B and RHS 145D.

Lateral branches/stems (flower stem):
*Shape of the branch in cross-section.*—Circular.
*Hollowness of the branch.*—Absent.
*Length.*—26.0 cm to 30.0 cm.
*Diameter.*—0.2 cm.
*Internode length.*—1.0 cm to 5.5 cm.
*Internode quantity per branch/stem.*—5 to 6 up to breaking point of the flower stem.
*Node length.*—0.3 cm to 0.4 cm.
*Node diameter.*—0.5 cm.
*Texture.*—Smooth.
*Color.*—Closest RHS N189A.
*Flower clustering on the lateral branch.*—None.

Foliage:
*Arrangement.*—Opposite, sheathing and spiraling up the stem.
*Length.*—11.0 to 13.0 cm.
*Width.*—0.4 cm.
*Shape.*—Linear.
*Apex.*—Acute.
*Base.*—Decurrent.
*Margin.*—Entire.
*Texture (both upper and lower surfaces).*—Smooth.
*Cross-section of the leaf.*—Flat to very weakly concave.
*Curvature of the leaf.*—Absent or very weakly concave.
*Glaucosity of the leaf.*—Medium to strong.
*Leaf color (both immature and mature).*—Immature: Upper surface: RHS 189B. Lower surface: RHS 189B. Mature: Upper surface: RHS 189A. Lower surface: RHS 189A.
*Venation pattern.*—Absent.

Flowers:
*Flower type and habit.*—Double, polypetalous.
*Fragrance.*—Present, medium to strong.
*Position of the flowers compared to the foliage of the plant.*—Far above.
*Profile of both the upper and lower part in the lateral view.*—Flat convex for the upper part and flat convex to convex for the lower part.
*Diameter of the flower.*—4.5 to 5.0 cm.
*Natural flowering season.*—May to October.
*Number of flowers per spray.*—3 to 4.
*Flower longevity on the plant.*—10 to 20 days.

Buds (before cracking color):
*Length.*—2.1 cm.
*Diameter.*—1.2 cm.
*Shape.*—Obovate.
*Color.*—Upper part between RHS 143A and C, lower part RHS 144D.
*Extrusion of the styles at the bud stage.*—Absent.

Corolla:
*Quantity of petals and arrangement.*—45 to 60 petals, persistent, apopetalous and overlapping.
*Corolla height.*—1.5 to 2.0 cm.
*Petal length.*—3.8 to 4.0 cm.
*Petal width.*—2.0 to 2.4 cm.
*Petal shape.*—Fan shaped.
*Petal apex.*—Obtuse.
*Petal base.*—Acute.
*Petal margin.*—Crenate-dentate.
*Number of petal margin incisions.*—Few.
*Depth of petal margin.*—Shallow.
*Petal texture (both upper and lower surfaces).*—Smooth, with a few creased/folded petals and sparse stetose-shaped extrusions throughout.
*Petal color.*—Immature: Upper surface: RHS 3C. Lower surface: RHS 3D. Mature: Upper surface: RHS 2C. Lower surface: RHS 3D.
*Stripes.*—Present, predominantly on upper surface but also visible on lower surface, two colors, a medium amount of the color RHS 26C and a few of the color RHS 46D.
*Speckles.*—Present, few, predominantly on upper surface but also visible on lower surface, color RHS 26C.
*Macule.*—present.

Calyx:
*Quantity of sepals and arrangement.*—Composed of 5 sepals, fused up to 1 cm below the apex.
*Longitudinal axis of the lobes of the calyx.*—Convex.
*Shape.*—Flat convex.
*Calyx height.*—2.4 to 2.6 cm.
*Calyx diameter (at the apex).*—1.4 to 1.8 cm.
*Calyx splitting.*—Observed occasionally.
*Calyx anthocyanin.*—Absent.
*Sepal texture (both upper and lower surfaces).*—Smooth.
*Sepal color.*—Upper surface: RHS 137B at the apex and RHS 141D at the base. Lower surface: RHS 145C.
*Position of the outer lobes of the epicalyx in relation to the calyx.*—Adpressed.
*Apex shape of the outer lobes of the epicalyx.*—Acute.
*Tip length of the outer lobes of the epicalyx.*—Short.
*Position of the inner lobes of the epicalyx in relation to the calyx.*—Adpressed.
*Apex shape of the inner lobes of the epicalyx.*—Acute.
*Tip length of the inner lobes of the epicalyx.*—Short.
*Epicalyx length.*—0.7 cm to 1.0 cm.
*Epicalyx width.*—0.7 cm to 1.2 cm.
*Color of epicalyx surface.*—Upper surface: RHS 137A. Lower surface: RHS 137D.

Pedicel:
Average length.—4.5 cm to 7.0 cm.
*Surface texture.*—Smooth.
*Color.*—RHS N189A.

Reproductive organs:
*Stamens.*—Quantity per flower: 15 to 30, some are fused along the filament with free anthers. Stamen petaloids: 10 to 15. Filament length: 2.0 to 2.2 cm. Filament color: RHS NN155C. Anther length: 0.3 cm. Anther diameter: 0.2 cm. Anther color: RHS 4C (before dehiscence). Anther attachment and shape: Some are dorsifixed, and some are basifixed and sagittate. Pollen amount: Low.

*Pistil*.—Quantity per flower: 1 with 2 to 3 styles per flower. Length: 2.7 to 3.0 cm.

*Stigma*.—Color: RHS 155B. Shape: Linear and hairy along the style. Length: 1.0 to 1.5 cm. Diameter: 0.1 cm.

*Style*.—Color: RHS NN155D. Length: 2.0 to 3.0 cm. Diameter: 0.1 cm.

*Ovary*.—Size: 0.7 cm in length and 0.6 cm in diameter. Shape: Rhombic. Color: RHS 145B on the apical half and RHS 145D on the basal half.

Seeds: Not observed to date.

Disease and insect resistance: No particular disease or insect resistance observed to date.

COMPARISON OF 'KLEDA28842' WITH PARENTAL LINE AND KNOWN VARIETY

'KLEDA28842' is distinguished from the known female parent as described in Table 1.

TABLE 1

| Comparison with Parental Line | | | |
|---|---|---|---|
| Trait or characteristic | 'KLEDA28842' | Female parent '16.895' (unpatented) | Male parent '16.886' (unpatented) |
| Flower color and pattern | Yellow flower color with a moderate amount of light orange stripes, a few pink-red stripes and a few pink-red speckles | Orange with darker orange stripes and flecks | Light orange, self |

TABLE 1-continued

'KLEDA28842' can be compared to the commercial *Dianthus* variety 'WP19 VAL01' (U.S. Plant Pat. No. 33,311). Differences between the varieties are described in Table 2.

TABLE 2

| Comparison with Similar Variety | | |
|---|---|---|
| Trait or characteristic | 'KLEDA28842' | 'WP19 VAL01' (U.S. Plant Pat. No. 33,311) |
| Main flower color and pattern | Yellow flower color with a moderate amount of light orange stripes, a few pink-red stripes and a few pink-red speckles | Yellow RHS 1D, self |
| Number of petals per flower | More than 'WP19 VAL01' | Less than 'KLEDA28842' |

I claim:

1. A new and distinct cultivar of *Dianthus* plant named 'KLEDA28842' as shown and described herein.

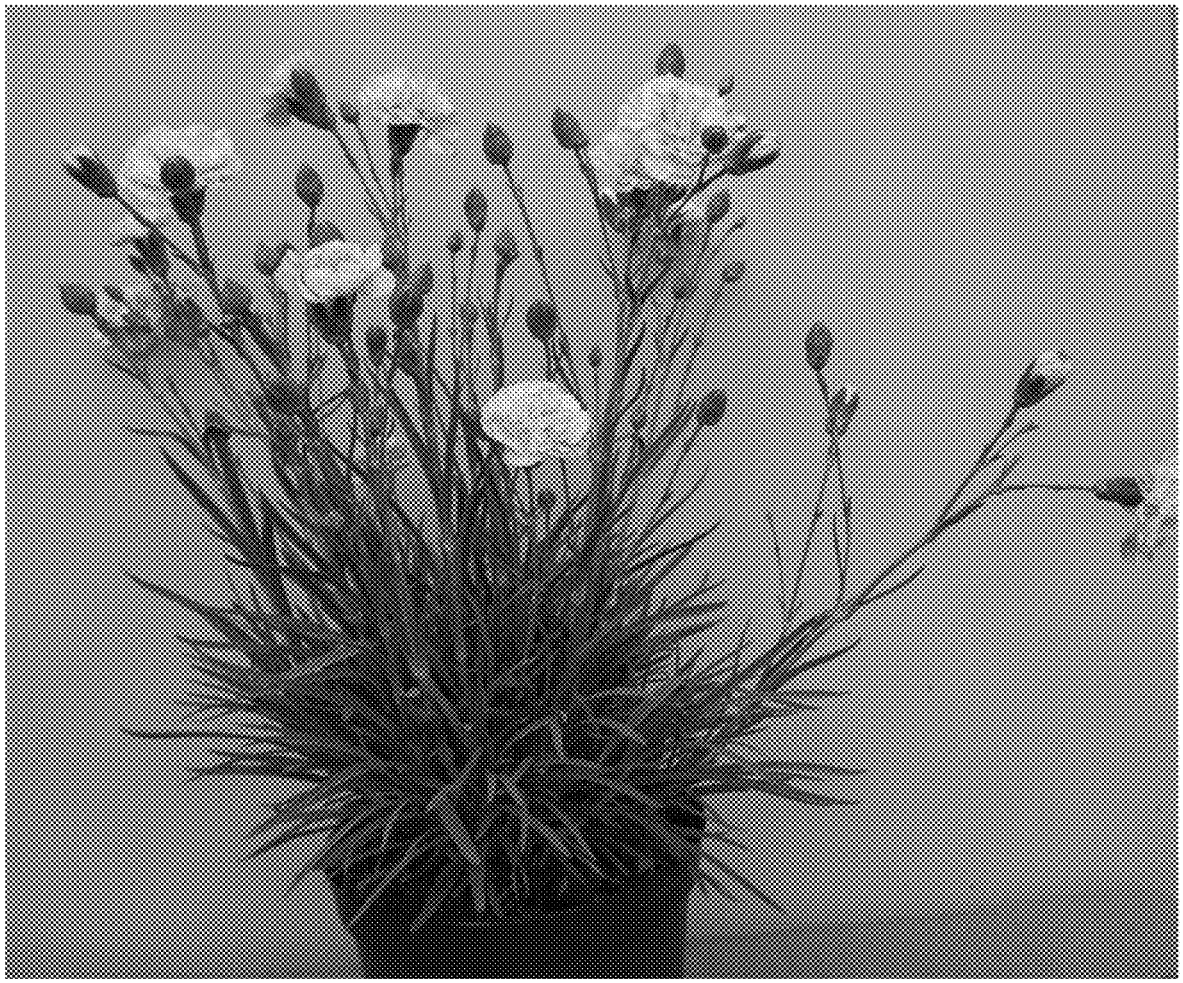

* * * * *